United States Patent
Lauritzen et al.

(10) Patent No.: US 10,479,781 B2
(45) Date of Patent: Nov. 19, 2019

(54) PEPTIDYL NITRIL COMPOUNDS AS DIPEPTIDYL PEPTIDASE I INHIBITORS

(71) Applicant: Prozymex A/S, Hørsholm (DK)

(72) Inventors: Conni Lauritzen, Rødovre (DK); John Pedersen, Nivå (DK)

(73) Assignee: Neuprozyme Therapeutics APS, Hørsholm (DK)

( * ) Notice: Subject to any disclaimer, the term of this patent is extended or adjusted under 35 U.S.C. 154(b) by 129 days.

(21) Appl. No.: 15/554,514

(22) PCT Filed: Mar. 4, 2016

(86) PCT No.: PCT/EP2016/054674
§ 371 (c)(1),
(2) Date: Aug. 30, 2017

(87) PCT Pub. No.: WO2016/139351
PCT Pub. Date: Sep. 9, 2016

(65) Prior Publication Data
US 2018/0044328 A1    Feb. 15, 2018

(30) Foreign Application Priority Data
Mar. 5, 2015   (EP) ..................................... 15157811

(51) Int. Cl.
*C07D 405/12* (2006.01)
*C07D 309/14* (2006.01)

(52) U.S. Cl.
CPC ......... *C07D 405/12* (2013.01); *C07D 309/14* (2013.01)

(58) Field of Classification Search
CPC ........................... C07D 405/12; C07D 309/14
USPC ....................................................... 514/254.1
See application file for complete search history.

(56) References Cited

FOREIGN PATENT DOCUMENTS

| WO | WO 2009/074829 A1 | 6/2009 |
|---|---|---|
| WO | WO 2010/128324 A1 | 11/2010 |
| WO | WO 2010/142985 A1 | 12/2010 |
| WO | WO 2011/154677 A1 | 12/2011 |
| WO | WO 2012/119941 A1 | 9/2012 |
| WO | WO 2012/130299 A1 | 10/2012 |
| WO | WO 2013/041497 A1 | 3/2013 |
| WO | WO 2014/140075 A1 | 9/2014 |
| WO | WO 2015/032945 A1 | 3/2015 |
| WO | WO 2016/139351 A1 | 9/2016 |

OTHER PUBLICATIONS

Adkison, A., et al., Dipeptidyl peptidase I activates neutrophil-derived serine proteases and regulates the development of acute experimental arthritis, *The Journal of Clinical Investigation*, 2002, vol. 109(3), pp. 363-371.
Berge, S., et al., "Pharmaceutical Salts," *Journal of Pharmaceutical Sciences*, 1977, vol. 66(1), pp. 1-19.
Bondebjerg, J., et al., "Diopeptidyl nitriles as human dipeptidyl peptidase I inhibitors," *Bioganic & Medicinal Chemistry Letters*, 2006, vol. 16, pp. 3614-3617.
Méthot, N, et al., "Inhibition of the Activation of Multiple Serine Proteases with a Cathepsin C Inhibitor Requires Sustained Exposure to Prevent Pro-enzyme Processing," *Journal of Biological Chemistry*, 2007, vol. 282(29), pp. 20836-20846.
Méthot, N, et al., "In Vivo Inhibition of Serine Protease Processing Requires a High Fractional Inhibition of Cathepsin C," *Molecular Pharmacology*, 2008, vol. 73(6), pp. 1857-1865.
Pham, C., et al., "Papillon-Lefevre Syndrome: Correlating the Molecular, Cellular, and Clinical Consequences of Cathepsin C/Dipeptidyl Peptidase I Deficiency in Humans," *The Journal of Immunology*, 2004, vol. 173(12), pp. 7277-7281.
Robichard, J., et al., A Novel Class of Nonpeptidic Biaryl Inhibitors of Human Cathepsin K, *J. Med. Chem*, 2003, vol. 46, pp. 3709-3727.
Yabin, Y., et al., "Research Progress of Dipeptidyl Peptidase I," *Chinese Journal of Clinical Pharmacology and Therapeutics*, 2006, vol. 11(6), pp. 601-605.
Zeng, G., et al., "Chathepsins: Structures, Functions and Inhibitors," *Acta Botanica Yunnanica*, 2005, vol. 27(4), pp. 337-354.

*Primary Examiner* — Kristin A Vajda
(74) *Attorney, Agent, or Firm* — Womble Bond Dickinson (US) LLP

(57) ABSTRACT

The invention relates to compounds of Formula (I) and their use as selective dipeptidyl peptidase I inhibitors, as well as pharmaceutical compositions comprising said compounds, and methods of treatment involving said compounds.

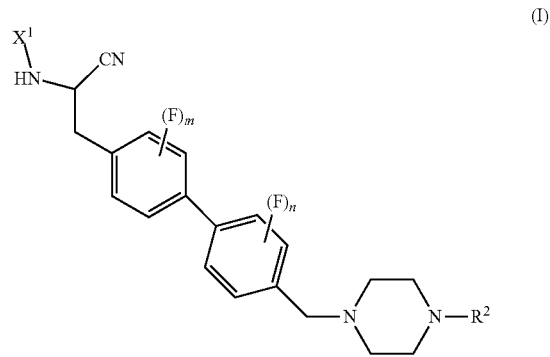

20 Claims, No Drawings

PEPTIDYL NITRIL COMPOUNDS AS DIPEPTIDYL PEPTIDASE I INHIBITORS

CROSS-REFERENCE TO RELATED APPLICATIONS

This application is a national stage filing under 35 U.S.C. 371 of PCT/EP2016/054674 filed Mar. 4, 2016, which International Application was published by the International Bureau in English on Sep. 9, 2016, and application claims priority from European Application No. 15157811.9, filed Mar. 5, 2015, which applications are hereby incorporated in their entirety by reference in this application.

FIELD OF THE INVENTION

The present invention relates to peptidyl nitril compounds in which the biphenyl moiety is substituted with one or more fluorine atoms, and their use as inhibitors of dipeptidyl peptidase I, pharmaceutical compositions containing the same, and methods of using the same agents for treatment and/or prevention of inflammatory diseases in which dipeptidyl peptidase I is involved, especially inflammatory diseases mediated by mast cells and neutrophil cells, e.g. chronic obstructive pulmonary disease and other respiratory diseases.

BACKGROUND OF THE INVENTION

Dipeptidyl peptidase I (DPPI; EC 3.4.14.1) also known as cathepsin C is a lysosomal cysteine peptidase belonging to the papain family. The enzyme is constitutively expressed in many tissues with highest levels in lung, kidney, liver and spleen. The cDNAs encoding rat, human and murine DPPI have been cloned and sequenced and it has been shown that the enzyme is highly conserved. DPPI is synthesized as an inactive precursor (Zymogen), and is activated by a non-autocatalytic excision of an internal activation peptide within the N-terminal propeptide. DPPI is the only member of the papain family that is functional as a tetramer, consisting of four identical subunits. Each is composed of an N-terminal fragment (the residual propart), a heavy chain and a light chain. Once activated, DPPI catalyzes the removal of dipeptides from the N-terminal end of polypeptide substrates with broad specificity. The pH optimum lies in the region of pH 5-7 using human DPPI. Recent data suggests that, beside of being an important enzyme in lysosomal protein degradation, DPPI also functions as a key enzyme in the activation of granule serine peptidases in neutrophils (cathepsin G, proteinase 3, neutrophil serine protease 4 and elastase), mast cells (chymase and tryptase) and cytotoxic T lymphocytes and natural killer cells (granzymes A and B).

Mast cells are found in many tissues, but are present in greater numbers along the epithelial linings of the body, such as the skin, respiratory tract and gastrointestinal tract. Mast cells are also located in the perivascular tissue surrounding small blood vessels. In humans, two types of mast cells have been identified; the T-type, which expresses only tryptase, and the MC-type, which expresses both tryptase and chymase. In humans, the T-type mast cells are located primarily in alveolar tissue and intestinal mucosa while the TC-type cells predominate in skin and conjuctiva. Mast cells can release a range of potent inflammatory mediators including cytokines, leukotrienes, prostaglandins, histamine and proteoglycans, but among the most abundant products of mast cell activation are the serine peptidases of the chymotrypsin family; tryptase and chymase. These peptidases are situated in the mast cell lysosomes as fully active enzymes. The exact site of tryptase and chymase activation from zymogen precursors is not known, but the Golgi apparatus might play a role in that regard. DPPI, which is particular abundant in mast cells, seems to be the key enzyme responsible for activation of chymase and tryptase. Moreover, tryptase and chymase are emerging as important mediators of allergic diseases such as asthma, inflammatory bowel disease and psoriasis. After secretion from activated mast cells, there is evidence that these peptidases are heavily involved in processes of inflammation, tissue remodelling, bronchoconstriction and mucus secretion, which have made these peptidases attractive for therapeutic intervention.

Neutrophils cause considerable damage in a number of pathological conditions. When activated, neutrophils secrete destructive granular enzymes including elastase, proteinase 3 and cathepsin G and undergo oxidative bursts to release reactive oxygen intermediates. Numerous studies have been conducted on each of these activating agents in isolation. Pulmonary emphysema, COPD, cystic fibrosis, idiopathic pulmonary fibrosis, alpha-1 antitrypsin deficiency, psoriasis, sepsis and rheumatoid arthritis are just some examples of pathological conditions associated with the potent enzymes elastase, proteinase 3 and cathepsin G.

The strong evidence associating tryptase, chymase, elastase, cathepsin G and other similar inflammatory peptidases with inflammatory diseases, points out DPPI as an attractive target enzyme for therapeutic intervention against the above mentioned diseases and other similar inflammatory diseases, due to its central role in activating these peptidases (Adkison et al. 2002, J. Clin. Invest, 109, 363-271; Pham. et al. 2004, J. Immunol, 173,7277-7281).

WO2012130299 and WO2012119941 to PROZYMEX disclose nitrile compounds and use thereof as dipeptidyl peptidase inhibitors. WO 2009074829A1 to Astrazeneca also discloses peptidyl nitriles and use thereof as dipeptidyl peptidase inhibitors. WO 2010128324A1, WO154677A1 and WO 2010142985A1 to Astrazeneca discloses further nitrile compounds and use thereof as dipeptidyl peptidase inhibitors WO2013041497A1 to Boehringer Ingelheim International GMBH discloses nitrile compounds as dipeptidyl peptidase inhibitors. Nathalie Méthot, Daniel Guay, Joel Rubin, Diane Ethier, Karen Ortega, Simon Wong, Denis Normandin, Christian Beaulieu, T. Jagadeeswar Reddy, Denis Riendeau, and M. David Percival: In Vivo Inhibition of Serine protease Processing Requires a High Fractional Inhibition of Cathepsin C, Mol Pharmacol 73:1857-1865, 2008 disclose dipeptide nitrile cathepsin C inhibitors. Nathalie Méthot, Joel Rubin, Daniel Guay, Christian Beaulieu, Diane Ethier T. Jagadeeswar Reddy, Denis Riendeau, and M. David Percival: Inhibition of the Activation of Multiple Serine proteases with a Cathepsin C Inhibitor Requires Sustained Exposure to Prevent Pro-enzyme Processing J. Biol. Chem., Vol. 282, Issue 29, 20836-20846, Jul. 20, 2007 disclose dipeptide nitrile cathepsin C inhibitors. Jon Bondebjerg, Henrik Fuglsang, Kirsten Rosendal Valeur, John Pedersen and Lars Nærum, Dipeptidyl nitriles as human dipeptidyl peptidase I inhibitors, Bioorganic & Medicinal Chemistry Letters 16 (2006) 3614-3617 disclose compounds having a dipeptide nitrile scaffold as inhibitors of human dipeptidyl peptidase I.

Object of the Invention

It is an object of the invention to provide novel compounds being inhibitors of dipeptidyl peptidase I, suitable for treatment of inflammatory diseases, cancers and infections.

SUMMARY OF THE INVENTION

The present invention relates to a compound of the formula (I):

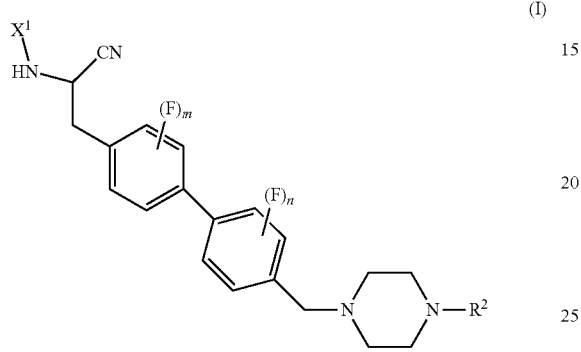

wherein
n is 0, 1 or 2 and m is 0, 1 or 2; such that the sum of m and n is 1, 2, 3 or 4;
F is fluoro;
$X^1$ represents

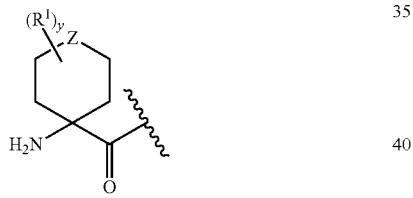

wherein y represents 0, 1, 2, 3, 4, 5, 6, 7 or 8
wherein Z represents O (oxygen);
when y is 1 or 2, then $R^1$ independently represents deuterium; halogen; hydroxyl; cyano; oxo (=O); mercapto; or $C_{1-3}$-alkyl; which $C_{1-3}$-alkyl is optionally substituted with at least one substituent selected from halogen, hydroxyl, cyano and mercapto;
or when y represents 3, 4, 5, 6, 7 or 8, then $R^1$ represents deuterium;
wherein $R^2$ represents —$C_{3-6}$-cycloalkyl, —$C_{1-3}$-alkyl-$C_{3-6}$-cycloalkyl or —$C_{1-6}$-alkyl, which —$C_{1-6}$-alkyl is optionally substituted with at least one substituent selected from hydroxyl, cyano or amino; and pharmaceutically-acceptable salts, solvates and hydrates thereof.
$R^2$ may be —$C_{1-6}$-alkyl, which —$C_{1-6}$-alkyl is optionally substituted with at least one substituent selected from hydroxyl, cyano or amino. Suitably, $R^2$ is —$C_{1-6}$-alkyl, preferably —$C_{1-3}$-alkyl, more preferably methyl-, ethyl- or propyl-. Suitably, y=0 or 1, preferably 0.
In one aspect of the compounds of Formula (I), m+n=1. In particular, m may be 1. In another aspect, m and n in Formula (I) are both 1. In another aspect, m is 2. Suitably, F is located at the 2-position and 2'-positions of the biphenyl moiety.

The following compounds are of particular interest:

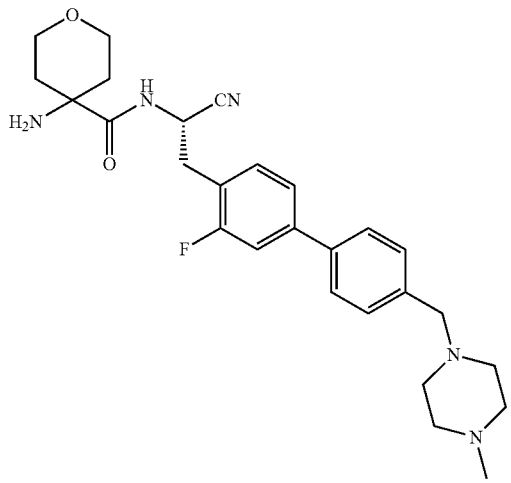

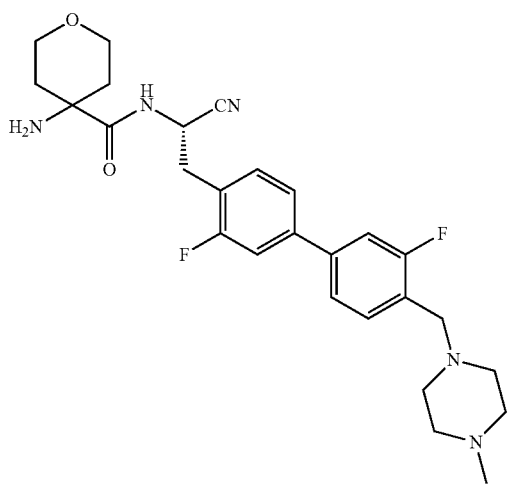

The following compounds are also of particular interest:

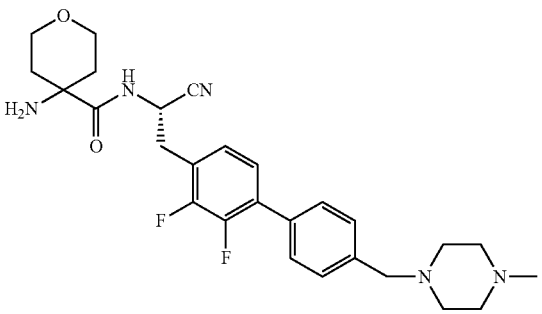

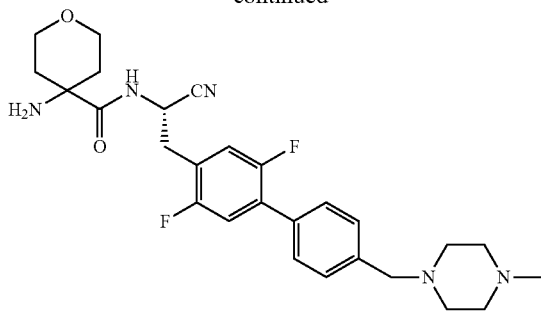

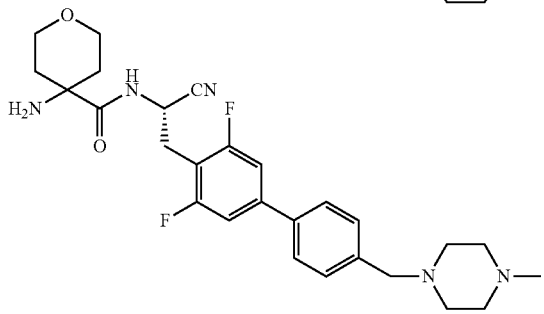

The term "DPPI" as used herein is intended to mean dipeptidyl peptidase I (EC 3.4.14.1) also known as cathepsin C, cathepsin J, dipeptidyl aminopeptidase I and dipeptidyl transferase. DPPI cleaves a dipeptide Xaa-Xbb from the N terminus of a polypeptide chain Xaa-Xbb-Xcc-[Xxx]$_n$, except when Xaa is Arg or Lys, or when Xbb or Xcc is Pro.

In the formulas, the group —CN is a nitrile group (—C≡N).

The wavy line in depicted substituents as e.g.

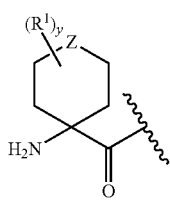

is used to indicate the bond, which is connected to the core molecule (formula I) as defined.

In the context of the present specification, unless otherwise stated, an alkyl substituent group or an alkyl moiety in a substituent group may be linear or branched.

The term "treatment" is defined as the management and care of a patient for the purpose of combating the disease, condition, or disorder and includes the administration of the compound of the present invention to prevent the onset of the symptoms or the complications, or alleviating the symptoms or the complications, or eliminating the disease, condition, or disorder.

"Half-life" (or "half-lives") refers to the time required for half of a quantity of a substance to be converted to another chemically distinct specie in vitro or in vivo.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

The compounds according to Formula (I) contain one or more asymmetric centers (also referred to as a chiral center) and may, therefore, exist as individual enantiomers, diastereomers, or other stereoisomeric forms, or as mixtures thereof. Chiral centers may also be present in a substituent such as an alkyl group. Where the stereochemistry of a chiral center present in Formula (I) or in any chemical structure illustrated herein, is not specified the structure is intended to encompass any stereoisomer and all mixtures thereof. Thus, compounds according to Formula (I)) containing one or more chiral center may be used as racemic mixtures, enantiomerically enriched mixtures, or as enantiomerically pure individual stereoisomers.

Individual stereoisomers of a compound according to Formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation. If there is a cycloalkyl group present, some substituent patterns may result in and axial or an equatorial configuration. Both forms are included, unless specified otherwise.

All tautomeric forms are also included in Formula (I), whether such tautomers exist in equilibrium or predominately in one form.

Preferred are the above compounds of formula (I), in their enantiomerically pure form of formula (II):

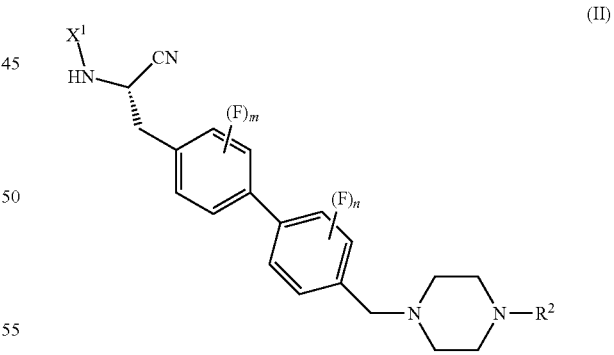

(II)

wherein $X^1$, $R^2$, m, n and F are as defined above.

The skilled artisan will appreciate that pharmaceutically-acceptable salts of the compounds according to Formula (I) may be prepared. Indeed, in certain embodiments of the invention, pharmaceutically-acceptable salts of the compounds according to Formula (I) may be preferred over the non-salt form because such salts impart greater stability or solubility to the molecule thereby facilitating formulation into a dosage form. Accordingly, the invention is further directed to pharmaceutically-acceptable salts of the compounds according to Formula (I). All details regarding the compounds of formula (I) are also relevant for the pharmaceutical composition.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycerophosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically-acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In the solid state, the compound of the invention can exist in crystalline, semi-crystalline and amorphous forms, as well as mixtures thereof. The skilled artisan will appreciate that pharmaceutically-acceptable solvates of the compound of the invention may be formed wherein solvent molecules are incorporated into the solid-state structure during crystallization. Solvates may involve water or non-aqueous solvents, or mixtures thereof. In addition, the solvent content of such solvates can vary in response to environment and upon storage. For example, water may displace another solvent over time depending on relative humidity and temperature. Solvates wherein water is the solvent that is incorporated into the solid-state structure are typically referred to as "hydrates." Solvates wherein more than one solvent is incorporated into the solid-state structure are typically referred to as "mixed solvates". Solvates include "stoichiometric solvates" as well as compositions containing variable amounts of solvent (referred to as "non-stoichiometric solvates"). Stoichiometric solvates wherein water is the solvent that is incorporated into the solid-state structure are typically referred to as "stoichiometric hydrates", and non-stoichiometric solvates wherein water is the solvent that is incorporated into the solid-state structure are typically referred to as "non-stoichiometric hydrates". The invention includes both stoichiometric and non-stoichiometric solvates.

In addition, crystalline forms of the compounds of the invention, including solvates thereof, may contain solvent molecules, which are not incorporated into the solid-state structure. For example, solvent molecules may become trapped in the crystals upon isolation. In addition, solvent molecules may be retained on the surface of the crystals. The invention includes such forms.

The compound of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, optic, intravaginal, and intranasal administration.

The compound of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for the compound of the invention depend on the pharmacokinetic properties of that compound, such as absorption, distribution, and half-life, which can be determined by the skilled artisan. In addition, suitable dosing regimens, including the amount administered and the duration such regimens are administered, for the compound of the invention depend on the condition being treated, the severity of the condition being treated, the age and physical condition of the patient being treated, the medical history of the patient to be treated, the nature of concurrent therapy, the particular route of administration chosen, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Typical daily dosages range from 1 mg to 1000 mg.

The compound of the invention may be administered as a prodrug. As used herein, a "prodrug" of the compound of the invention is a functional derivative of the compound which, upon administration to a patient, eventually liberates the compound of the invention in vivo. Administration of the compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In both drug discovery and drug development, prodrugs have become an established tool for improving physicochemical, biopharmaceutical or pharmacokinetic properties of pharmacologically active agents that overcome barriers to a drug's usefulness.

Coupling of short peptides or single amino acids as carriers of a therapeutic agent can be used as an effective type of prodrug approach. In this approach an amino acid or a di- (or oligo)peptide moiety is linked to a free (primary or secondary) amino group of the drug through an amide bond, that can be specifically cleaved by an endogenous peptidase, e.g. dipeptidyl peptidase IV (DPPIV/CD26), dipeptidyl peptidase I (DPPI/cathepsin C), aminopeptidase N (APN/CD13), pyroglutamyl aminopeptidase, proline iminopeptidase, aminopeptidase P, elastase, cathepsin G, proteinase 3, tryptase or chymase.

The amino acid or a di- or oligo-peptide moiety can consist of proteinogenic amino acids (i.e. amino acids that occur naturally in proteins) or non-proteinogenic amino acids (i.e. non-proteinogenic amino acids that either occur naturally or are chemically synthesized).

In one aspect, the compound disclosed herein is linked via a free (primary or secondary) amino group to an amino acid or a di- (or oligo)peptide moiety. These prodrugs may be converted to the desired active compound by a peptidase catalyzed reaction.

Starting materials and reagents are either commercially-available or may be prepared by one skilled in the art using methods described in the literature.

Compounds of the invention according to Formula (I), e.g.

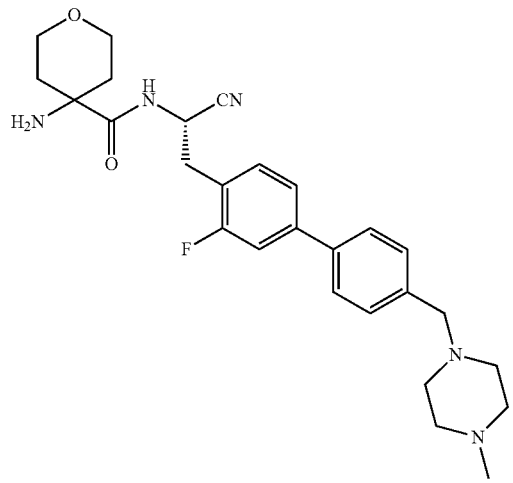

Compound PZ1101 can be made essentially as described in the following synthetic scheme

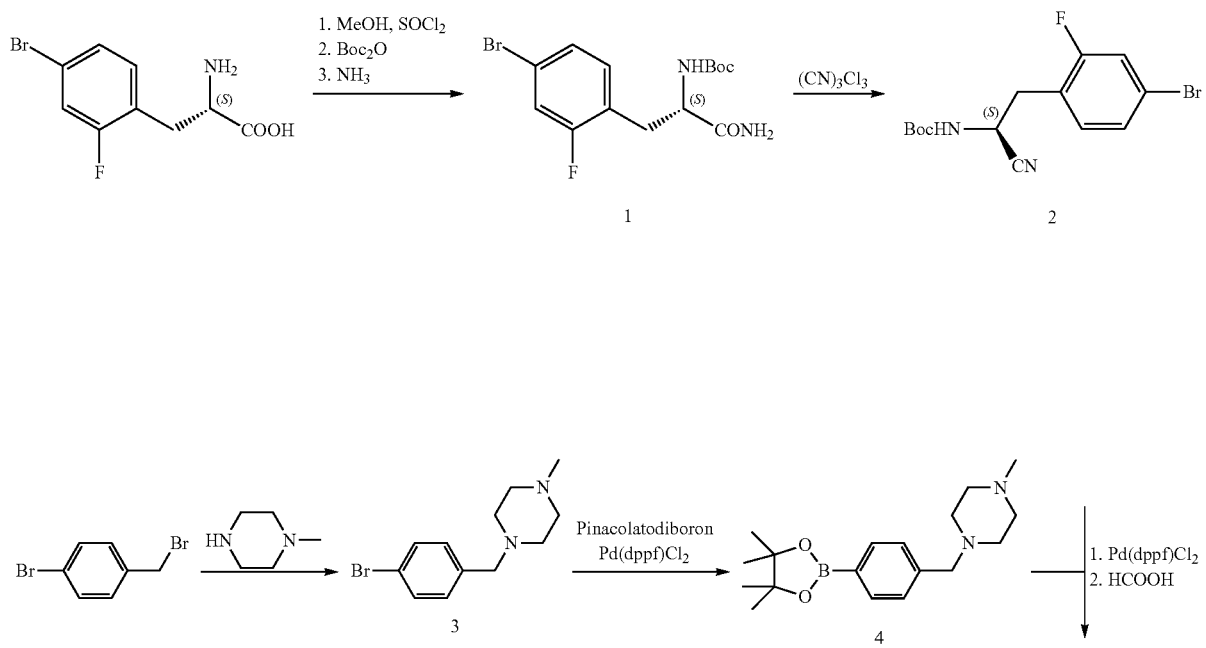

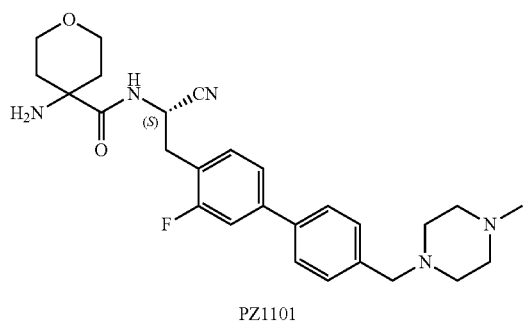

PZ1101

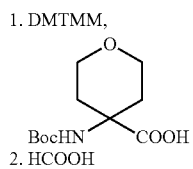

1. DMTMM,
2. HCOOH

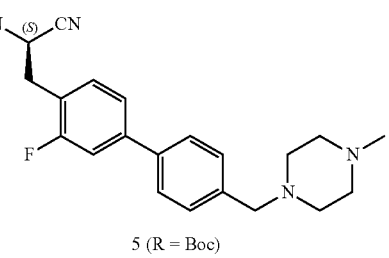

5 (R = Boc)
6 (R = H)

Compounds of the invention according to Formula (I) in which m=2, e.g.

Compound PZ1118

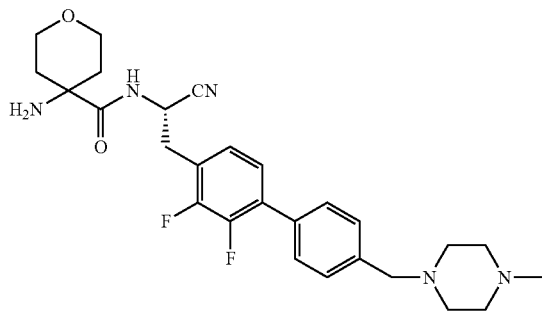

can for example be synthesized essentially as described for synthesis of PZ1101 in Example 1, using

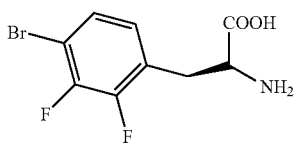

as starting material.

The compounds of general formula I may be used on their own or combined with other active substances of formula I according to the invention. The compounds of general formula I may optionally also be combined with other pharmacologically active substances. These include, B2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRLI modulators, LTB4-receptor (BLTI, BLT2) antagonists, Histamine HI receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, J K1, J K2, J K3 or SAP, inhibitors of the NF-κB signalling pathway as for example IKK2 kinase inhibitors, iNOS inhibitors, MRP4 inhibitors or leukotriene biosynthese inhibitors.

The compounds disclosed herein will normally, but not necessarily, be formulated into a pharmaceutical composition prior to administration to a patient. Accordingly, in another aspect a pharmaceutical composition comprising, as an active substance, the compound as disclosed herein or a pharmaceutically acceptable salt thereof together with a pharmaceutically acceptable adjuvant, carrier or diluent, is provided.

The pharmaceutical compositions disclosed herein may be prepared and packaged in bulk form wherein a safe and effective amount of the compound disclosed herein can be extracted and then given to the patient such as with powders, syrups, and solutions for injection. Alternatively, the pharmaceutical compositions disclosed herein may be prepared and packaged in unit dosage form wherein each physically discrete unit contains a safe and effective amount of the compound as disclosed herein. When prepared in unit dosage form, the pharmaceutical compositions disclosed herein typically contain from 1 mg to 1000 mg.

The pharmaceutical compositions disclosed herein typically contain one compound as disclosed herein. However, in certain embodiments, the pharmaceutical compositions of the invention may optionally further comprise one or more additional pharmaceutically active compounds. Conversely, the pharmaceutical compositions of the invention typically contain more than one pharmaceutically-acceptable excipient. However, in certain embodiments, the pharmaceutical compositions of the invention contain one pharmaceutically-acceptable excipient.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable. The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company). In one aspect, the invention is directed to a solid oral dosage form such as a tablet or capsule comprising a safe and effective amount of the compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc. In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise the compound of the invention as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides.

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation. Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape.

Aerosols may be formed by suspending or dissolving the compound of the invention in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising the compound of the invention will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Suspensions and solutions comprising the compound of the invention may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of the invention may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds according to Formula I are prepared using conventional organic syntheses. Suitable synthetic routes are depicted below in the following general reaction schemes. Starting materials and reagents depicted below in the general reaction schemes are commercially available or can be made from commercially available starting materials using methods known by those skilled in the art.

The compounds disclosed herein may be converted to a pharmaceutically acceptable salt thereof, preferably an acid addition salt such as a hydrochloride, hydro bromide, trifluoroacetate, sulphate, phosphate, acetate, fumarate, maleate, tartrate, lactate, citrate, pyruvate, succinate, oxalate, methane sulphonate or p-toluenesulphonate. The compound of formula (1) and pharmaceutically acceptable salts thereof may exist in solvated, for example hydrated, as well as unsolvated forms, and the present invention encompasses all such solvated forms. In a further aspect, the compound disclosed herein is in the form of a pharmaceutically acceptable salt thereof.

In a further aspect, the compounds disclosed herein are for use in medicine such as for use as a dipeptidyl peptidase I (DPPI) inhibitor. In one aspect, they have activity as pharmaceuticals, in particular as inhibitors of dipeptidyl peptidase I activity, and thus may be used in the treatment of:

Obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); acute lung injury; acute respiratory distress syndrome; bronchitis, including infectious and eosinophilic bronchitis; emphysema; bronchiectasis; cystic fibrosis; alpha-1 antitrypsin deficiency; sarcoidosis; farmer's lung and related diseases; hypersensitivity pneumonitis; lung fibrosis, including cryptogenic fibrosing alveolitis, idiopathic pulmonary fibrosis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; psoriasis, atopic dermatitis, contact dermatitis or other eczematous dermatoses, and delayed-type hypersensitivity reactions; phyto- and photodermatitis; seborrhoeic dermatitis; dermatitis herpetiformis, lichen planus; lichen sclerosus et atrophica; pyoderma gangrenosum; skin sarcoid; discoid lupus erythematosus; pemphigus; pemphigoid; epidermolysis bullosa; urticaria; angioedema; vasculitides; toxic erythemas; cutaneous eosinophilias; alopecia areata; male-pattern baldness; Sweet's syndrome; Weber-Christian syndrome; erythema multiforme; cellulitis, both infective and non-infective; panniculitis; cutaneous lymphomas, non-melanoma skin cancer and other dysplastic lesions; drug-induced disorders including fixed drug eruptions; blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial; sepsis; nephritis including interstitial and glomerulonephritis; nephritic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female); acute and chronic implications following, for example, transplantation of kidney, heart, liver, lung, bone marrow, skin or cornea or following blood transfusion; or chronic graft versus host disease; rheumatoid arthritis; irritable bowel syndrome; inflammatory bowel disease; gout; pseudogout; Alzheimer's disease; systemic lupus erythematosus; multiple sclerosis; Hashimoto's thyroiditis; Graves' disease; Addison's disease; diabetes mellitus, including type-1 diabetes mellitus; idiopathic thrombocytopaenic purpura; eosinophilic fasciitis; hyper-1gE syndrome; antiphospholipid syndrome and Sazary syndrome; cancers with neutrophil involvement; treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; virus diseases such as genital warts, common warts, plantar warts, hepatitis B, hepatitis C, herpes simplex virus, molluscum contagiosum, variola, human immunodeficiency virus (H1V), human papilloma virus (HPV), cytomegalovirus (CMV), varicella zoster virus (VZV), rhinovirus, adenovirus, coronavirus, influenza, para-influenza; bacterial diseases such as tuberculosis and *mycobacterium avium*, leprosy; other infectious diseases, such as malaria, fungal diseases, *chlamydia, candida, aspergillus*, cryptococcal meningitis, pneumocystis camii, cryptosporidiosis, histoplasmosis, toxoplasmosis, trypanosome infection and leishmaniasis; congestive heart failure; atherosclerosis; coronary artery disease; myocardial infarction; reperfusion injury; abdominal aortic aneurysms (AAA); diabetic cardiomyopathy (DCM); hypertension; peripheral artery disease; cardiac arrhythmia; stroke and cardiomegaly.

In a further aspect, the compounds disclosed herein are for use as a dipeptidyl peptidase I inhibitor.

In a further aspect, the compounds or pharmaceutical compositions disclosed herein are for use in treating asthma, chronic obstructive pulmonary disease, bronchiectasis, cystic fibrosis, alpha-1 antitrypsin deficiency, idiopathic pulmonary fibrosis, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis.

In a further aspect, the compounds or pharmaceutical compositions disclosed herein are for use in treating asthma, chronic obstructive pulmonary disease, bronchiectasis, cystic fibrosis, alpha-1 antitrypsin deficiency, idiopathic pulmonary fibrosis, acute lung injury; acute respiratory distress syndrome, congestive heart failure, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis or sepsis.

In yet a further aspect, the compounds or pharmaceutical compositions disclosed herein are for use in treating asthma, chronic obstructive pulmonary disease, bronchiectasis, cystic fibrosis, alpha-1 antitrypsin deficiency, idiopathic pulmonary fibrosis, congestive heart failure, myocardial infarction, reperfusion injury, abdominal aortic aneurysms, diabetic cardiomyopathy, gout, pseudogout, respiratory syncytial virus infection, psoriasis, rheumatoid arthritis or sepsis.

For the above-mentioned therapeutic uses the dosage administered will, of course, vary with the compound employed, the mode of administration, the treatment desired and the disorder indicated.

In a further aspect, the pharmaceutical composition in unit dosage form, comprises from about 1 µg to about 1000 mg such as, e.g., from about 10 µg to about 500 mg, from about 0.05 to about 100 mg or from about 0.1 to about 50 mg, of the active substance.

In yet a further aspect, disclosed herein is a compound which 24 hours after a single subcutaneous animal dosing at a concentration of 10 µmol/kg, has a concentration in bone marrow of 250 nM or more, such as 500 nM or, 750 nM or more or 1000 nM or more.

In yet a further aspect, disclosed herein is a compound which 12 hours after a single subcutaneous animal dosing at a concentration of 10 µmol/kg, has a concentration in bone marrow of 1000 nM or more, such as 1500 nM or more, 2000 nM or more, 3000 nM or more, or 5000 nM or more.

In a further aspect, the pharmaceutical composition disclosed herein is for oral, nasal, transdermal, pulmonal or parenteral administration.

In one aspect, a method of treating an obstructive airways disease in a patient suffering from, or at risk of, said disease, which comprises administering to the patient a therapeutically effective amount of the compound of formula (I) or a pharmaceutically acceptable salt thereof, is provided herein.

In one aspect, a method for the treatment of ailments, the method comprising administering to a subject in need thereof an effective amount of the compound as disclosed herein or of a composition as disclosed herein, is provided.

In a further aspect, an effective amount of the compound as disclosed herein is in a range of from about 1 µg to about 1000 mg such as, e.g., from about 10 µg to about 500 mg, from about 0.05 to about 100 mg or from about 0.1 to about 50 mg per day.

In one aspect, the use of the compound or pharmaceutical composition as disclosed herein for the preparation of a medicament, is provided.

In one aspect, the use of the compound, a pharmaceutically acceptable salt thereof or pharmaceutical composition as disclosed herein for the preparation of a medicament for treating asthma, chronic obstructive pulmonary disease, bronchiectasis, cystic fibrosis, alpha-1 antitrypsin deficiency, idiopathic pulmonary fibrosis, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis, is provided.

In one aspect, the use of the compound, a pharmaceutically acceptable salt thereof or pharmaceutical composition as disclosed herein in the manufacture of a medicament for treating asthma, chronic obstructive pulmonary disease, bronchiectasis, cystic fibrosis, alpha-1 antitrypsin deficiency, idiopathic pulmonary fibrosis, acute lung injury, acute respiratory distress syndrome, congestive heart failure, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis or sepsis, is provided.

In one aspect, the use of the compound, a pharmaceutically acceptable salt thereof or pharmaceutical composition as disclosed herein in the manufacture of a medicament for treating asthma, chronic obstructive pulmonary disease, bronchiectasis, cystic fibrosis, alpha-1 antitrypsin deficiency, idiopathic pulmonary fibrosis, congestive heart failure, myocardial infarction, reperfusion injury, abdominal aortic aneurysms, diabetic cardiomyopathy, gout, pseudogout, respiratory syncytial virus infection, psoriasis, rheumatoid arthritis or sepsis is provided.

In one aspect, a method for modulating DPPI levels in a subject in need thereof comprising administering to said subject an amount of the compound or a pharmaceutically acceptable salt thereof as disclosed herein or a composition as disclosed herein in an amount effective to modulate said DPPI levels in said subject, is provided.

In one aspect, said DPPI is inhibited.

In one aspect, a combination of the compound or a pharmaceutically acceptable salt thereof as disclosed herein and one or more agents independently selected from: a non-steroidal glucocorticoid receptor agonist; a selective β2 adrenoceptor agonist; a phosphodiesterase inhibitor; a peptidase inhibitor; a glucocorticoid; an anticholinergic agent; a modulator of chemokine receptor function; and an inhibitor of kinase function, is provided.

In another aspect, a method for treatment of a medical condition selected from the group selected from asthma, chronic obstructive pulmonary disease, bronchiectasis, cystic fibrosis, alpha-1 antitrypsin deficiency, idiopathic pulmonary fibrosis, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis, is provided, said method comprising administration of a pharmaceutically effective amount of a compound of formula (I) or the composition according to the invention. Suitably, in this method, the medical condition is selected from the group selected from asthma, chronic obstructive pulmonary disease, bronchiectasis, cystic fibrosis, alpha-1 antitrypsin deficiency, idiopathic pulmonary fibrosis, congestive heart failure, myocardial infarction, reperfusion injury, abdominal aortic aneurysms, diabetic cardiomyopathy, gout, pseudogout, respiratory syncytial virus infection, psoriasis, rheumatoid arthritis or sepsis.

The invention relates to the following numbered aspects:

Aspect 1: A compound of the formula (I)

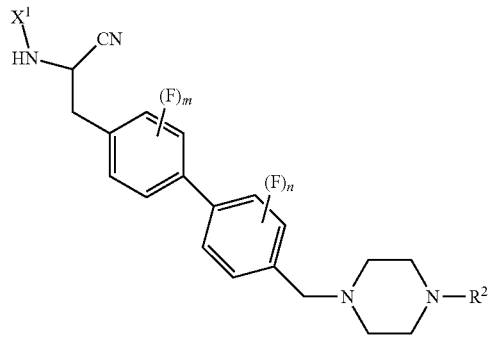

wherein n is 0, 1 or 2 and m is 0, 1 or 2; such that the sum of m and n is 1, 2, 3 or 4;

F is fluoro;

$X^1$ represents

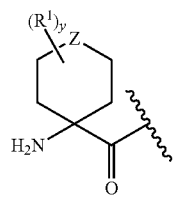

wherein y represents 0, 1, 2, 3, 4, 5, 6, 7 or 8;

wherein Z represents O (oxygen);

when y is 1 or 2, then $R^1$ independently represents deuterium; halogen; hydroxyl; cyano; oxo (=O); mercapto; or $C_{1-3}$-alkyl; which $C_{1-3}$-alkyl is optionally substituted with at least one substituent selected from halogen, hydroxyl, cyano and mercapto;

or when y represents 3, 4, 5, 6, 7 or 8, then $R^1$ represents deuterium;

wherein $R^2$ represents —$C_{3-6}$-cycloalkyl, —$C_{1-3}$-alkyl-$C_{3-6}$-cycloalkyl or —$C_{1-6}$-alkyl, which —$C_{1-6}$-alkyl is optionally substituted with at least one substituent selected from hydroxyl, cyano or amino as well as pharmaceutically-acceptable salts, solvates and hydrates thereof.

Aspect 2: The compound according to aspect 1, wherein $R^2$ is —$C_{1-6}$-alkyl, which —$C_{1-6}$-alkyl is optionally substituted with at least one substituent selected from hydroxyl, cyano or amino.

Aspect 3: The compound according to any one of the preceding aspects, wherein $R^2$ is —$C_{1-6}$-alkyl, preferably —$C_{1-3}$-alkyl, more preferably methyl-, ethyl- or propyl-.

Aspect 4: The compound according to any one of the preceding aspects, wherein y represents 0, 1, 2, 3 or 4, such as e.g. 0 or 1, preferably 0.

Aspect 5: The compound according to any one of the preceding aspects, being:

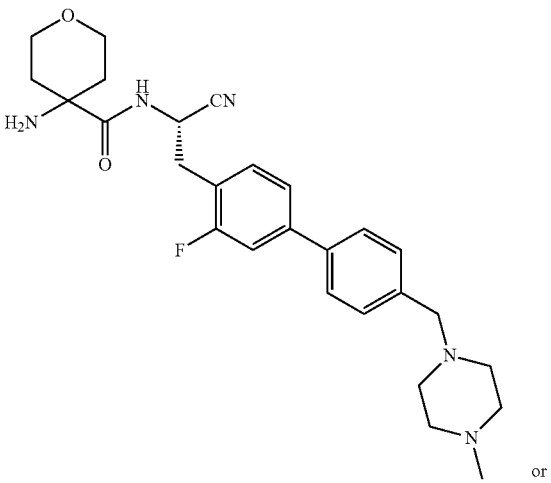

or

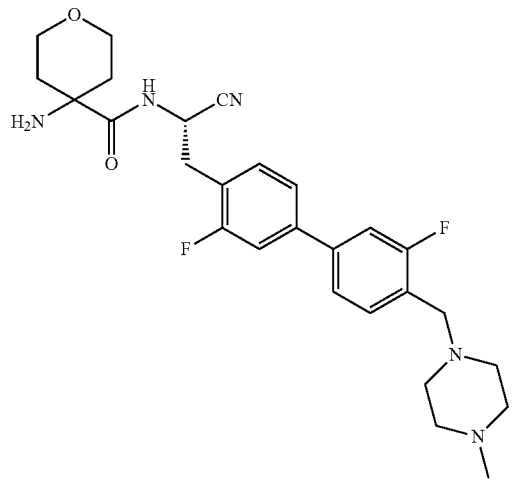

Aspect 6: The compound according to any one of the preceding aspects, in the enantiomerically pure form of formula (II):

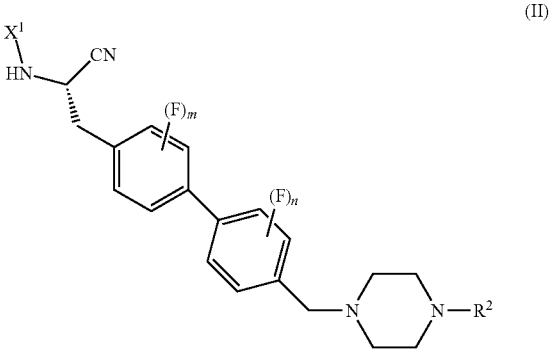

wherein $X^1$ and $R^2$ are as defined in any one of the preceding aspects.

Aspect 7. The compound according to any one of the preceding aspects, wherein m+n=1, preferably m=1; or m is 2; or m is 2 and n is preferably 0.

Aspect 8: A pharmaceutical composition comprising a compound of the formula (I) according to any one of aspects 1-7, or a pharmaceutically acceptable salt thereof, together with at least one pharmaceutically-acceptable adjuvant, carrier or diluent.

Aspect 9: A compound according to any one of aspects 1-7 or composition according to aspect 8 for use as a medicament.

Aspect 10: A compound according to any one of aspects 1-7 or composition according to aspect 8 for treating asthma, chronic obstructive pulmonary disease, bronchiectasis, cystic fibrosis, alpha-1 antitrypsin deficiency, idiopathic pulmonary fibrosis, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis.

Aspect 11: A compound according to any one of aspects 1-7 or composition according to aspect 8 for treating asthma, chronic obstructive pulmonary disease, bronchiectasis, cystic fibrosis, alpha-1 antitrypsin deficiency, idiopathic pulmonary fibrosis, congestive heart failure, myocardial infarction, reperfusion injury, abdominal aortic aneurysms, diabetic cardiomyopathy, gout, pseudogout, respiratory syncytial virus infection, psoriasis, rheumatoid arthritis or sepsis.

Aspect 12: A method for treatment of a medical condition selected from the group selected from asthma, chronic obstructive pulmonary disease, bronchiectasis, cystic fibrosis, alpha-1 antitrypsin deficiency, idiopathic pulmonary fibrosis, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis, said method comprising administration of a pharmaceutically effective amount of a compound of formula (I) according to any one of aspects 1-7 or composition according to aspect 8.

Aspect 13: The method according to aspect 12, wherein the medical condition is selected from the group selected from asthma, chronic obstructive pulmonary disease, bronchiectasis, cystic fibrosis, alpha-1 antitrypsin deficiency, idiopathic pulmonary fibrosis, congestive heart failure, myocardial infarction, reperfusion injury, abdominal aortic aneurysms, diabetic cardiomyopathy, gout, pseudogout, respiratory syncytial virus infection, rheumatoid arthritis or sepsis.

Aspect 14: Use of a compound of formula (I) according to any one of aspects 1-7 or composition according to aspect 8 for the manufacture of a medicament for the treatment of asthma, chronic obstructive pulmonary disease, bronchiectasis, cystic fibrosis, alpha-1 antitrypsin deficiency, idiopathic pulmonary fibrosis, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis.

Aspect 15: The use according to aspect 14, wherein the medicament is for the treatment of asthma, chronic obstructive pulmonary disease, bronchiectasis, cystic fibrosis, alpha-1 antitrypsin deficiency, idiopathic pulmonary fibrosis, congestive heart failure, myocardial infarction, reperfusion injury, abdominal aortic aneurysms, diabetic cardiomyopathy, gout, pseudogout, respiratory syncytial virus infection, psoriasis, rheumatoid arthritis or sepsis.

Materials and Methods

Cell Based DPPI Inhibition Assay 1

The herein described compounds are DPPI inhibitors, which indirectly inhibit the activity of serine peptidases that are activated by DPPI, such as elastase. Using the cell based assay described below, the biological activity of the compounds of the invention or other DPPI inhibitors may be determined.

Neutrophil elastase enzymatic activities in U937 cells grown in the presence of DPPI inhibitors were measured by methods modified from Méthot N; Rubin 3; Guay D; Beaulieu C; Ethier D; Reddy T J; Riendeau D and Percival M D (2007) J Biol Chem, 282, 20836-20846.

U937 cells were propagated in culture media (RPMI 1640, supplemented with 10% FBS, 10 mM Hepes, 1 mM sodium pyrovate, 100 units/ml of each of penicillin and streptomycin). Cells were seeded in 12-well plates at 0.4× $10^6$ cells/ml in volumes of 1.5 ml per well in the presence of no or increasing concentrations of DPPI inhibitor. 12 points in duplicate in the range of 0.1 nM to 50 µM inhibitor were tested. After 24 hours cells were harvested, washed with PBS and lysed in 20 mM Tris-HCl, pH 7.5, 100 mM NaCl, 0.2% Triton X-100. Debris was removed by centrifugation and supernatants were retained. The extracts were mixed with assay buffer (50 mM Tris, 0.1% Triton X-100, 0.5 M NaCl, pH 8.0) supplemented with substrate (MetOSuc-Ala-Ala-Pro-Val-pNA; Bachem; Cat. No. L-1335) to a final concentration of 0.9 mM.

The activity of neutrophil elastase was determined by measuring the enzymatic release of chromogenic p-nitroaniline from the substrate MetOSuc-Ala-Ala-Pro-Val-pNA, which leads to an increase in absorbance at 405 nm. Assays were carried out in 96-well plates in a final volume of 200 µL at 37° C., and absorbance was measured 8 times during 21-35 minutes using a plate reader. $IC_{50}$ was determined using a 4-parameter logistic equation in a non-linear curve fitting routine.

Cell Based DPPI Inhibition Assay 2

The herein described compounds are DPPI inhibitors, which indirectly inhibit the activity of serine peptidases that are activated by DPPI, such as elastase. Using the cell based assay described below, the biological activity of the compounds of the invention or other DPPI inhibitors may be determined.

Neutrophil elastase enzymatic activities in U937 cells grown in the presence of DPPI inhibitors were measured by methods modified from Méthot N; Rubin J; Guay D; Beaulieu C; Ethier D; Reddy T J; Riendeau D and Percival M D (2007) J Biol Chem, 282, 20836-20846.

U937 cells were propagated in culture media (RPMI 1640, supplemented with 10% FBS, 10 mM Hepes, 1 mM sodium pyrovate, 100 units/ml of each of penicillin and streptomycin). Cells were seeded in 12-well plates at ≈0.2× $10^6$ cells/ml in volumes of 1.5 ml per well in the presence of no or increasing concentrations of DPPI inhibitor. 12 points in duplicate in the range of 0.01 nM to 10 µM inhibitor were tested. After 48 hours cells were harvested, washed with PBS and lysed in 20 mM Tris-HCl, pH 7.5, 100 mM NaCl, 0.2% Triton X-100. Debris was removed by centrifugation and supernatants were retained. The extracts were mixed with assay buffer (50 mM Tris, 0.5 M NaCl, pH 7.5) supplemented with substrate (MetOSuc-Ala-Ala-Pro-Val-pNA; Bachem; Cat. No. L-1335) to a final concentration of 0.9 mM.

The activity of neutrophil elastase was determined by measuring the enzymatic release of chromogenic p-nitroaniline from the substrate MetOSuc-Ala-Ala-Pro-Val-pNA, which leads to an increase in absorbance at 405 nm. Assays were carried out in 96-well plates in a final volume of 200 μL at 37° C., and absorbance was measured 8 times during 21 minutes using a plate reader. $IC_{50}$ was determined using a 4-parameter logistic equation in a non-linear curve fitting routine.

Human DPPI Inhibition Assay 1

Using this assay, the $IC_{50}$ value of the compound of the invention may be determined using Gly-Phe-paranitroanilide as a DPPI specific substrate.

Assay buffer: 20 mM citric acid (2.1 g citric acid), 150 mM NaCl (4.4 g NaCl) and 2 mM EDTA (370 mg EDTA) was dissolved in 500 mL $H_2O$, and pH was adjusted to 4.5 with HCl.

Substrate: Gly-Phe-paranitroanilide (Sigma Aldrich; Cat. No G0142) was used as the substrate for determination of $IC_{50}$ values. Km was 2.2 mM. The substrate was solubilized in dimethylformamid to give a 0.2-0.5 M stock solution, which was then further diluted with stirring in assay buffer to a final concentration of 1 mM.

DPPI: Human DPPI (obtained from UNIZYME Laboratories A/S, DK-2970 Hørsholm, Denmark) was stored at −20° C. in a buffer containing 2.5 mM Na-phosphate, 150 mM NaCl, 2 mM cysteamine, 50% glycerol, pH 7.0 at a concentration of 1-2 mg/mL (5-10 μM). This stock solution was diluted 500-1000 times in assay buffer to a concentration of 10-20 nM.

Assay conditions: The assay was performed in 96-well plates. Diluted enzyme (25 μL) was added to the well, followed by 25 μL of test substance in varying concentrations, and the solution was mixed. The plate was incubated at 37° C. for 5 minutes, followed by addition of 150 μL of 1 mM substrate prewarmed to 37° C. (corresponding to a substrate concentration of 750 μM in the assay). The absorption was measured at 405 nm at 37° C. for every 90 seconds for 12 minutes or every 20 seconds for 4 minutes. Each measurement was made in duplicate. $IC_{50}$ was determined using a 4-parameter logistic equation in a non-linear curve fitting routine.

Human DPPI Inhibition Assay 2

Using this assay, the $IC_{50}$ value of the compound of the invention may be determined using Gly-Phe-paranitroanilide as a DPPI specific substrate.

Assay buffer: 20 mM citric acid (2.1 g citric acid), 150 mM NaCl (4.4 g NaCl) and 2 mM EDTA (370 mg EDTA) was dissolved in 500 mL $H_2O$, and pH was adjusted to 4.5 with HCl.

Substrate: Gly-Phe-paranitroanilide (Sigma Aldrich; Cat. No G0142) was used as the substrate for determination of $IC_{50}$ values. Km was 2.2 mM. The substrate was solubilized in dimethylformamid to give a 0.2-0.5 M stock solution, which was then further diluted with stirring in assay buffer to a final concentration of 1 mM.

DPPI: Human DPPI (obtained from UNIZYME Laboratories A/S, DK-2970 Hørsholm, Denmark) was stored at −20° C. in a buffer containing 2.5 mM Na-phosphate, 150 mM NaCl, 2 mM cysteamine, 50% glycerol, pH 7.0 at a concentration of 2.2 mg/mL (≈12 μM). This stock solution was diluted 800-3200 times in assay buffer to a concentration of about 4-15 nM.

Assay conditions: The assay was performed in 96-well plates. Diluted enzyme (25 μL) was added to the well, followed by 25 μL of test substance in varying concentrations, and the solution was mixed. The plate was incubated at 37° C. for 5 minutes, followed by addition of 150 μL of 1 mM substrate prewarmed to 37° C. (corresponding to a substrate concentration of 750 μM in the assay). The absorption was measured at 405 nm at 37° C. for every 90 seconds for 12 minutes or every 20 seconds for 4 minutes. Each measurement was made in duplicate. $IC_{50}$ was determined using a 4-parameter logistic equation in a non-linear curve fitting routine.

Test for Metabolic Stability

The test for metabolic stability was performed by Absorption System, Exton, Pa. 19341, USA.

The test compound (DPPI inhibitor) was dissolved in 100% DMSO at a concentration of 10 mM. The reaction mixture, consisted of Mouse or Human Liver Microsomes (1.0 mg/mL), 1 mM NADPH, 100 mM Potassium Phosphate, pH 7.4, 10 mM Magnesium Chloride and test compound at a concentration of 5 μM.

An aliquot of the reaction mixture (without cofactors) was incubated in a shaking water bath at 37° C. for 3 minutes. Another aliquot of the reaction mixture was prepared as the negative control. The test compound was added into both the reaction mixture and the negative control at a final concentration of 5 μM.

The reaction was initiated by the addition of NADPH to 1 mM (not into the negative controls) and then incubated in a shaking water bath at 37° C. Aliquots (100 μL) were withdrawn at 0, 10, 20, 30, and 60 minutes or at 0, 15, 30 and 60 minutes and combined with 900 μL of ice-cold 50/50 acetonitrile/$dH_2O$ to terminate the reaction. A control (testosterone) was run simultaneously with the test compound in a separate reaction. LC/MS/MS is used to determine the peak area response ratio (peak area corresponding to test compound or control divided by that of an analytical internal standard). The natural log of the percent remaining was plotted versus time. A linear fit was used to determine the rate constant. The fit was truncated if the percent remaining of test compound was less than 10%. The elimination half-lives associated with the disappearance of the test and control compounds were determined to compare their relative metabolic stability.

Abbreviations

PE/EA: Petroleum Ether/Ethyl Acetate

EA: Ethyl acetate

CAN: Acetonitrile

THF: Tetrahydrofuran

DMF: Dimethylformamide

MeOH: Methanol

TEA: Triethylamine

TFAA: Trifluoroacetic anhydride

DCM: Dichloromethane

Pd(dppf)$Cl_2$: [1,1'-Bis(diphenylphosphino)ferrocene]palladium(II) dichloride

DIEA: N,N-Diisopropylethylamine

TBTU: O-(Benzotriazol-1-yl)-N,N,N',N'-tetramethyluronium tetrafluoroborate

Boc: t-Butyloxycarbonyl r.t: Room temperature

EXAMPLE 1
(S)-4-amino-N-(1-cyano-2-(3-fluoro-4'-((4-methyl-piperazin-1-yl)methyl)-[1,1'-biphenyl]-4-yl)ethyl)tetrahydro-2H-pyran-4-carboxamide (PZ1101)
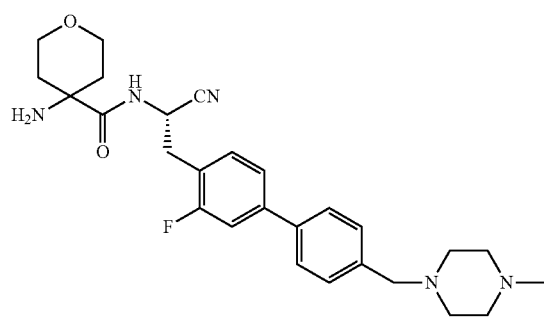
PZ1101
Synthetic Scheme
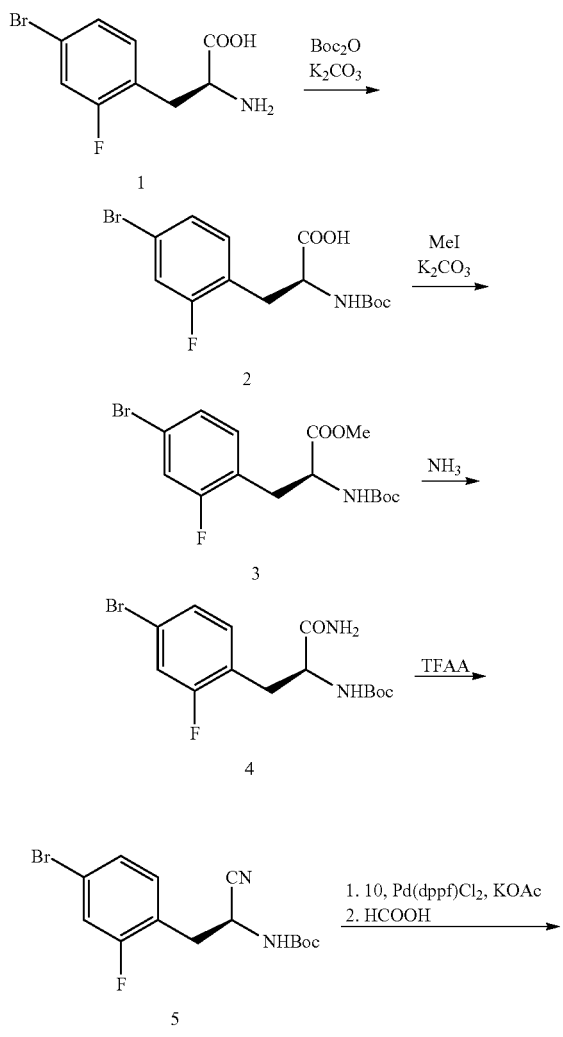
-continued
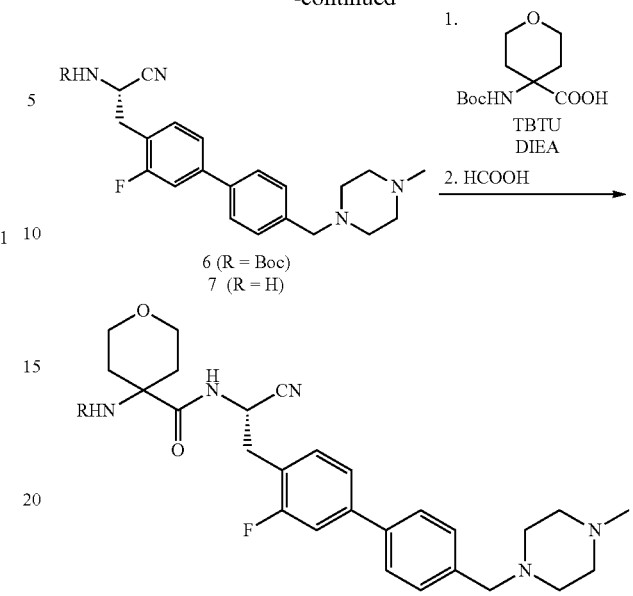
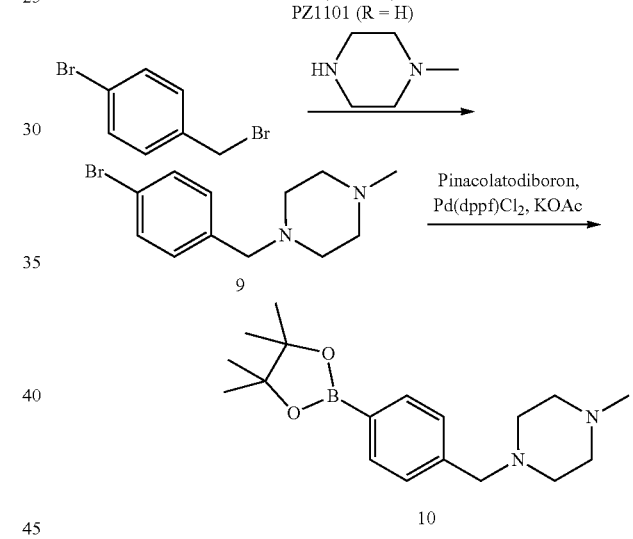
Procedure Description
Step-1
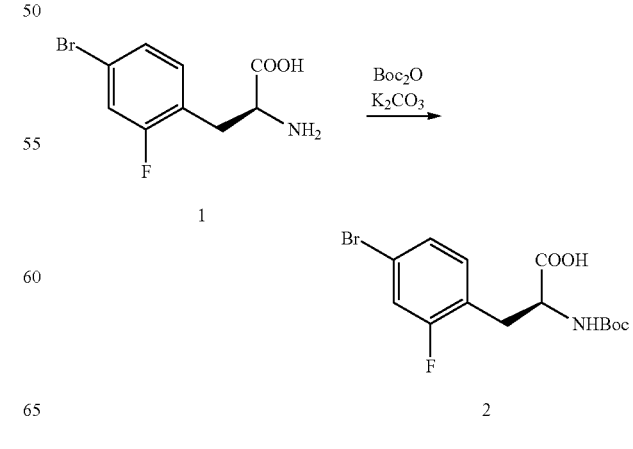

(S)-3-(4-bromo-2-fluorophenyl)-2-(tert-butoxycarbonylamino)propanoic acid (2)

To a solution of compound 1 (30 g, 114.5 mmol, 1.0 eq) in THF/water (200 mL/200 mL) were added K$_2$CO$_3$ (47.4 g, 343.5 mmol, 3.0 eq) and Boc$_2$O (30 g, 137.4 mmol, 1.2 eq). The reaction was stirred at r.t. for 2 hr. After completion, the pH was adjusted to 2 to 3 and the solution was extracted with EA twice. The combined organics were washed with brine, dried over anhydrous Na$_2$SO$_4$ and concentrated to afford compound 2 (45 g, 50% in 3 steps) as a white solid. The crude solid was used for the next step without purification. $^1$H-NMR (400 MHz, CDCl$_3$): δ 9.81 (br, 2H), 7.24-7.22 (d, J=7.6 Hz, 4H), 7.05-7.10 (m, 2H), 6.97-6.98 (m, 1H), 5.03-5.05 (d, J=8.0 Hz, 1H), 4.44-4.61 (m, 2H), 3.23-3.32 (m, 2H), 2.84-3.06 (m, 2H), 1.40 (s, 9H), 1.27 (s, 9H); MS (ESI): m/z 360.22 [M−H]−.

Step-2

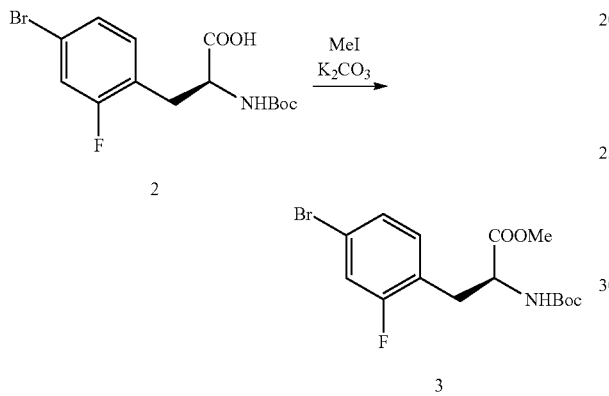

(S)-methyl 3-(4-bromo-2-fluorophenyl)-2-(tert-butoxycarbonylamino)propanoate (3)

To a solution of crude compound 2 (45 g, 124.3 mmol, 1.0 eq) in DMF (400 mL) were added K$_2$CO$_3$ (51.5 g, 372.9 mmol, 3.0 eq) and methyl iodide (MeI) (15.5 mL, 248.6 mmol, 2.0 eq). The reaction was stirred at r.t. for 30 min. After completion, the reaction was diluted with EA. The solution was washed with water and brine, dried over anhydrous Na$_2$SO$_4$ and concentrated to give compound 3 (48.5 g, 100%) as a light yellow oil. The crude oil was used for the next step without purification.

Step-3

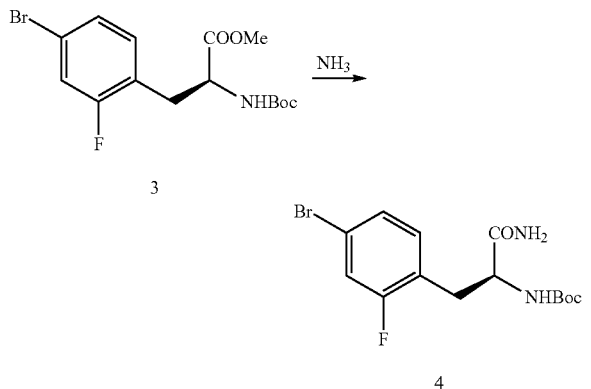

(S)-tert-butyl 1-amino-3-(4-bromo-2-fluorophenyl)-1-oxopropan-2-ylcarbamate (4)

A solution of compound 3 (48.5 g) in MeOH (400 mL) was bubbled with NH$_3$ (g) at −50° C. for 20 min. Then the reaction was stirred at r.t. overnight. After completion, the reaction was concentrated to give a white solid. The crude product was suspended in PE/EA (10:1) and filtered to afford compound 4 (25g, 53.7%) as a white solid.

Step-4

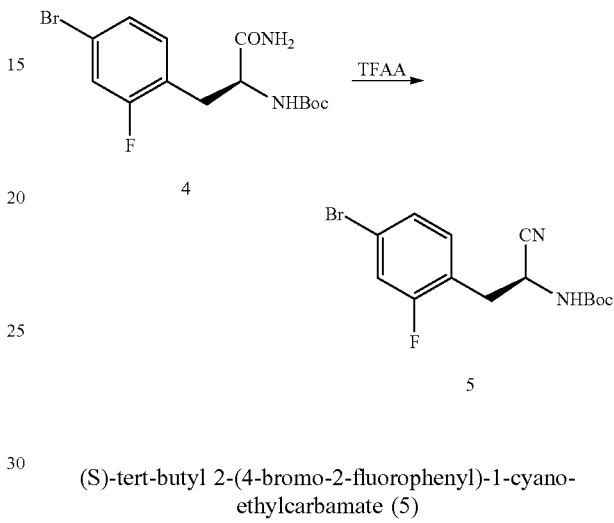

(S)-tert-butyl 2-(4-bromo-2-fluorophenyl)-1-cyanoethylcarbamate (5)

To a suspension of compound 4 (25 g, 69.3 mmol, 1.0 eq) in DCM (600 mL) were added TEA (40.3 mL, 290.9 mmol, 4.2 eq) and TFAA (21.5 mL, 152.4 mmol, 2.2 eq) at 0° C. The reaction was stirred at r.t. for 2 hr. After completion, the reaction was washed with water twice, dried over anhydrous Na$_2$SO$_4$ and concentrated to give a light yellow solid. The crude solid was recrystallized in PE/EA (500 mL/50 mL) and filtered. The filtrate was dried at reduced pressure to afford compound 5 (17 g, 71.6%) as a white solid.

Step-5

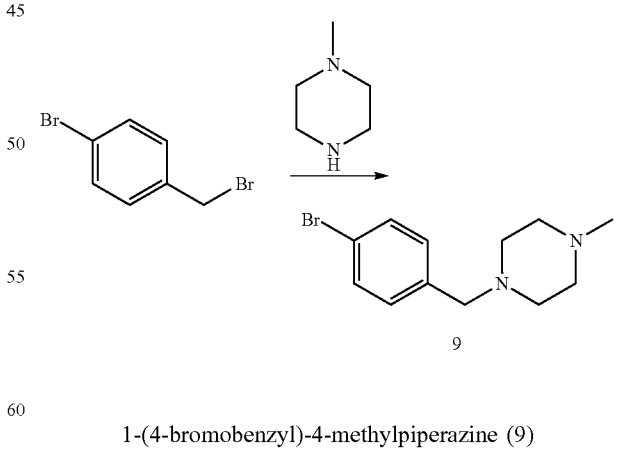

1-(4-bromobenzyl)-4-methylpiperazine (9)

A solution of 1-bromo-4-(bromomethyl)benzene (20 g, 0.08 mol, 1.0 eq) in DCM (80 mL) was added dropwise slowly to a solution of 1-methylpiperazine (16 g, 0.16 mol, 2.0 eq) in DCM (160 mL) and the reaction was stirred at r.t. for 2 hr. After completion, the reaction was quenched with water and filtered. The filtrate was separated and the aqueous layer was extracted with DCM once more. The combined organics were dried over anhydrous Na$_2$SO$_4$ and concentrated to afford compound 9 (16.5 g, 76.7%) as a light yellow liquid. $^1$H-NMR (400 MHz, CDCl$_3$): δ 7.72-7.74 (d, J=8.4 Hz, 1H), 7.54-7.56 (d, J=8.4 Hz, 1H), 7.49-7.51 (d, J=8.4 Hz, 1H), 7.26-7.28 (d, J=8.4 Hz, 1H), 4.61 (s, 1H), 3.59 (s, 1H), 3.29-3.50 (m, 2H), 2.94-2.97 (m, 2H), 2.63-2.85 (m, 2H).

Step-6

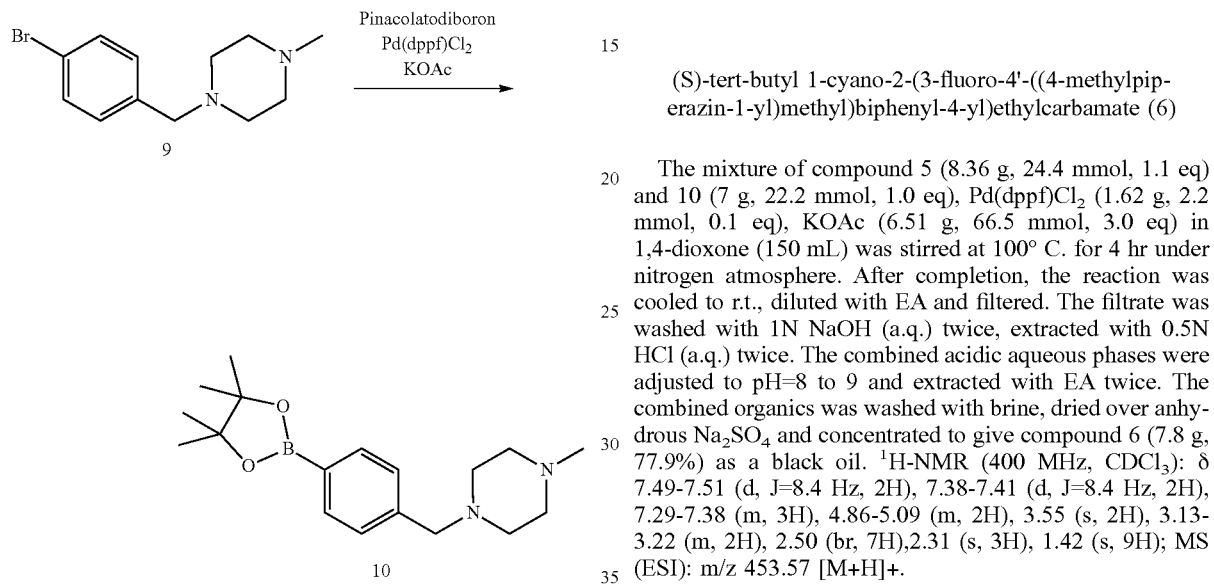

1-methyl-4-(4-(4,4,5,5-tetramethyl-1,3,2-dioxaborolan-2-yl)benzyl)piperazine (10)

The mixture of compound 9 (16.5 g, 61.3 mmol, 1.0 eq), pinacolatodiboron (17.1 g, 67.5 mmol, 1.1 eq), KOAc (18.0 g, 184 mmol, 3.0 eq) and Pd(dppf)Cl$_2$ (1.35 g, 1.84 mmol, 0.03 eq) in 1,4-dioxane (240 mL) was stirred at 110° C. for 3 hr under nitrogen atmosphere. After completion, the reaction was cooled to r.t., diluted with EA and filtered. The filtrate was washed with brine twice, dried over anhydrous Na$_2$SO$_4$ and concentrated. The residue was purified by flash silica-gel column chromatography to give compound 10 (14.6 g, 75.3%) as an earth yellow solid. $^1$H-NMR (400 MHz, CDCl$_3$): δ 7.75-7.77 (d, J=8.0 Hz, 2H), 7.31-7.33 (d, J=8.0 Hz, 2H), 3.58 (s, 2H), 2.69-2.80 (m, 8H), 2.52 (s, 3H), 1.34 (s, 12H).

Step-7 and 8

(S)-tert-butyl 1-cyano-2-(3-fluoro-4'-((4-methylpiperazin-1-yl)methyl)biphenyl-4-yl)ethylcarbamate (6)

The mixture of compound 5 (8.36 g, 24.4 mmol, 1.1 eq) and 10 (7 g, 22.2 mmol, 1.0 eq), Pd(dppf)Cl$_2$ (1.62 g, 2.2 mmol, 0.1 eq), KOAc (6.51 g, 66.5 mmol, 3.0 eq) in 1,4-dioxone (150 mL) was stirred at 100° C. for 4 hr under nitrogen atmosphere. After completion, the reaction was cooled to r.t., diluted with EA and filtered. The filtrate was washed with 1N NaOH (a.q.) twice, extracted with 0.5N HCl (a.q.) twice. The combined acidic aqueous phases were adjusted to pH=8 to 9 and extracted with EA twice. The combined organics was washed with brine, dried over anhydrous Na$_2$SO$_4$ and concentrated to give compound 6 (7.8 g, 77.9%) as a black oil. $^1$H-NMR (400 MHz, CDCl$_3$): δ 7.49-7.51 (d, J=8.4 Hz, 2H), 7.38-7.41 (d, J=8.4 Hz, 2H), 7.29-7.38 (m, 3H), 4.86-5.09 (m, 2H), 3.55 (s, 2H), 3.13-3.22 (m, 2H), 2.50 (br, 7H), 2.31 (s, 3H), 1.42 (s, 9H); MS (ESI): m/z 453.57 [M+H]+.

(S)-2-amino-3-(3-fluoro-4'-((4-methylpiperazin-1-yl)methyl)biphenyl-4-yl)propanenitrile (7)

The solution of compound 6 (7.8 g, 17.3 mmol) in formic acid (98%, 40 mL) was stirred at r.t. overnight. After completion, the reaction was poured into ice cold saturated aqueous NaHCO$_3$. The solution was adjusted to pH=9 to 10, extracted with EA three times. The combined organics were washed with brine, dried over anhydrous Na$_2$SO$_4$ and concentrated. The residue was purified by flash silica gel column chromatography to give crude compound 7 (4.5g, 74.1%) as a yellow oil. $^1$H-NMR (400 MHz, CDCl$_3$): δ 7.49-7.51 (d, J=8.4 Hz, 2H), 7.38-7.41 (d, J=8.4 Hz, 2H), 7.29-7.38 (m, 3H), 4.00-4.04 (m, 1H), 3.55 (s, 2H), 3.11-3.13 (m, 1H), 2.50 (br, 6H), 2.31 (s, 3H), 1.98 (br, 2H), 1.69-1.71 (m, 1H); MS (ESI): m/z 353.22 [M+H]+.

Step-9 and 10

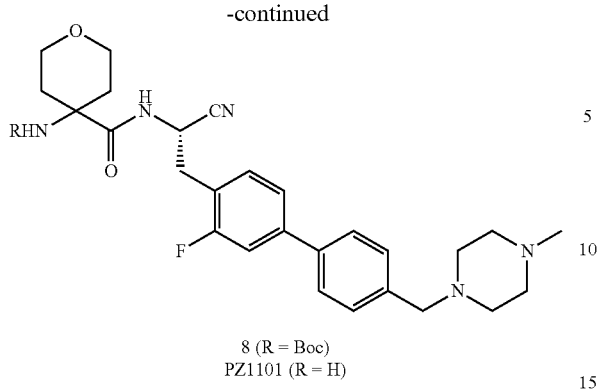

8 (R = Boc)
PZ1101 (R = H)

(S)-tert-butyl 4-(1-cyano-2-(3-fluoro-4'-((4-methyl-piperazin-1-yl)methyl)biphenyl-4-yl)ethylcarbamoyl)tetrahydro-2H-pyran-4-ylcarbamate (8)

The solution of compound 7 (500 mg, 1.42 mmol, 1.0 eq) and 4-(tert-butoxycarbonylamino)tetrahydro-2H-pyran-4-carboxylic acid (418 mg, 1.7 mmol, 1.2 eq) in THF (10 mL) was stirred at 0° C. for 30 min. Then TBTU (684 mg, 2.13 mmol, 1.5 eq) and DIEA (0.5 mL, 2.84 mmol, 2.0 eq) were added. The reaction was stirred at 0° C. for 1 hr, warmed to r.t. and stirred for another 4 hr. After completion, the reaction was diluted with EA and water, and separated. The organic layer was washed with saturated aqueous $NaHCO_3$ twice, brine once, dried over anhydrous $Na_2SO_4$ and concentrated. The residue was purified by preparative HPLC to give compound 8 (445 mg, 45%) as a white solid. $^1$H-NMR (400 MHz, $CDCl_3$): δ 7.81 (br, 1H), 7.50-7.52 (d, J=8.4 Hz, 2H), 7.38-7.40 (d, J=8.0 Hz, 2H), 7.29-7.36 (m, 3H), 5.11-5.15 (m, 1H), 4.74 (m, 1H), 3.77-3.79 (m, 1H), 3.61-3.67 (m, 2H), 3.59 (s, 3H), 3.17-3.22 (m, 2H), 2.67 (br, 6H), 2.46 (s, 3H), 1.79-2.24 (m, 4H), 1.43 (s, 9H); MS (ESI): m/z 580.53 [M+H]+.

(S)-4-amino-N-(1-cyano-2-(3-fluoro-4'-((4-methyl-piperazin-1-yl)methyl)-[1,1'-biphenyl]-4-yl)ethyl) tetrahydro-2H-pyran-4-carboxamide (PZ1101)

The solution of compound 8 (445 mg) in formic acid (98%, 5 mL) was stirred at 20° C. for 24 hr. After completion, the reaction solution was added dropwise to ice cold saturated aqueous $NaHCO_3$. The solution was adjusted to pH 9 to 10 by aqueous NaOH and extracted with EA five times. The combined organics were dried over anhydrous $Na_2SO_4$ and concentrated. The residue was purified by preparative HPLC to afford PZ1101 (230 mg, 62.5%) as a white solid. $^1$H-NMR (400 MHz, $CDCl_3$): δ 8.29-8.31 (d, J=8.8 HZ, 1H), 7.49-7.51 (d, J=8.0 Hz, 2H), 7.39-7.41 (d, J=8.0 Hz, 2H), 7.28-7.41 (m, 3H), 5.14-5.16 (m, 1H), 3.82-3.88 (m, 2H), 3.55-3.61 (m, 4H), 3.17-3.25 (m, 2H), 2.52 (br, 8H), 2.00-2.45 (m, 7H); $^{19}$F-NMR (376 MHz, $CDCl_3$): δ −117.14; MS (ESI): m/z 480.4 [M+H]+; HPLC: RT=4.206, 98.32%.

PZ1101 was found to have an $IC_{50}$ of ≈6 nM in the Human DPPI inhibition assay 2 and an $IC_{50}$ of ≈2.5 nM in the cell based DPPI inhibition assay 2. Furthermore, PZ1101 has a half-life in human liver microsomes of more than 120 minutes.

The invention claimed is:
1. A compound of the formula (I)

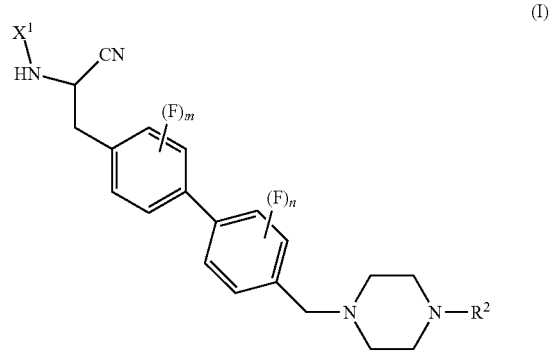

wherein n is 0, 1 or 2 and m is 0, 1 or 2; such that the sum of m and n is 1, 2, 3 or 4;
F is fluoro;
$X^1$ represents

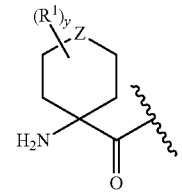

wherein y represents 0, 1, 2, 3, 4, 5, 6, 7 or 8;
wherein Z represents O (oxygen);
when y is 1 or 2, then $R^1$ independently represents deuterium; halogen; hydroxyl; cyano; oxo (=O); mercapto; or $C_{1-3}$-alkyl; which $C_{1-3}$-alkyl is optionally substituted with at least one substituent selected from halogen, hydroxyl, cyano and mercapto;
or when y represents 3, 4, 5, 6, 7 or 8, then $R^1$ represents deuterium;
wherein $R^2$ represents —$C_{3-6}$-cycloalkyl, —$C_{1-3}$-alkyl-$C_{3-6}$-cycloalkyl or —$C_{1-6}$-alkyl, which —$C_{1-6}$-alkyl is optionally substituted with at least one substituent selected from hydroxyl, cyano or amino; as well as pharmaceutically-acceptable salts, solvates and hydrates thereof.

2. The compound of claim 1, wherein the compound is:

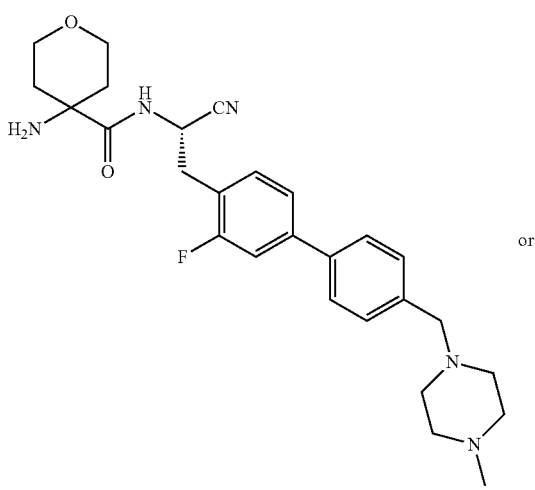

or

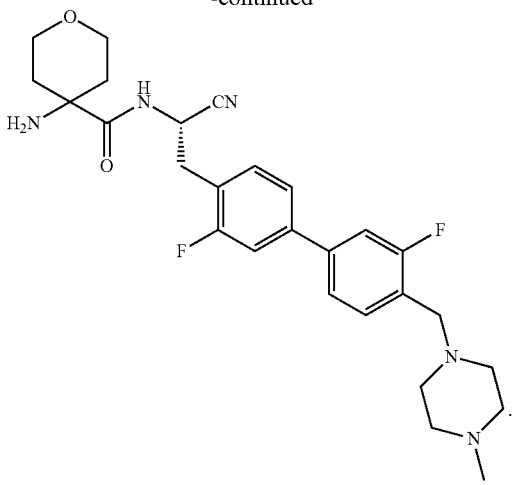

3. The compound of claim 1, wherein $R^2$ is —$C_{1-6}$-alkyl, which —$C_{1-6}$-alkyl is optionally substituted with at least one substituent selected from hydroxyl, cyano or amino.

4. The compound of claim 1, wherein $R^2$ is —$C_{1-6}$-alkyl.

5. The compound of claim 1, wherein y represents 0, 1, 2, 3 or 4.

6. The compound of claim 1, wherein m+n=1.

7. The compound of claim 1, wherein m=2.

8. A pharmaceutical composition comprising the compound of formula (I) of claim 1, or a pharmaceutically acceptable salt thereof, and at least one pharmaceutically-acceptable adjuvant, carrier or diluent.

9. The compound of claim 1 for use as a medicament.

10. The compound of claim 1 for treating asthma, chronic obstructive pulmonary disease, bronchiectasis, cystic fibrosis, alpha-1 antitrypsin deficiency, idiopathic pulmonary fibrosis, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis.

11. The compound of claim 1 for treating asthma, chronic obstructive pulmonary disease, bronchiectasis, cystic fibrosis, alpha-1 antitrypsin deficiency, idiopathic pulmonary fibrosis, congestive heart failure, myocardial infarction, reperfusion injury, abdominal aortic aneurysms, diabetic cardiomyopathy, gout, pseudogout, respiratory syncytial virus infection, psoriasis, rheumatoid arthritis or sepsis.

12. A method for treatment of a medical condition selected from the group consisting of asthma, chronic obstructive pulmonary disease, bronchiectasis, cystic fibrosis, alpha-1 antitrypsin deficiency, idiopathic pulmonary fibrosis, acute lung injury, acute respiratory distress syndrome, congestive heart failure, atherosclerosis, myocardial infarction, reperfusion injury, abdominal aortic aneurysms, diabetic cardiomyopathy, gout, pseudogout, respiratory syncytial virus infection, inflammatory bowel diseases, psoriasis, rheumatoid arthritis, multiple sclerosis, malaria, Alzheimer's disease or sepsis, said method comprising administration of a pharmaceutically effective amount of the compound of claim 1.

13. The method of claim 12, wherein the medical condition is selected from the group consisting of asthma, chronic obstructive pulmonary disease, bronchiectasis, cystic fibrosis, alpha-1 antitrypsin deficiency, idiopathic pulmonary fibrosis, congestive heart failure, myocardial infarction, reperfusion injury, abdominal aortic aneurysms, diabetic cardiomyopathy, gout, pseudogout, respiratory syncytial virus infection, psoriasis, rheumatoid arthritis or sepsis.

14. The compound of claim 1, wherein $R^2$ is —$C_{1-3}$-alkyl.

15. The compound of claim 1, wherein $R^2$ is methyl-, ethyl- or propyl-.

16. The compound of claim 1, wherein y represents 0 or 1.

17. The compound of claim 1, wherein y represents 0.

18. The compound of claim 1, wherein m=1.

19. The compound of claim 1 for treating cystic fibrosis.

20. The method of claim 12, wherein the medical condition is cystic fibrosis.

* * * * *